United States Patent [19]

Walter

[11] Patent Number: 5,633,439
[45] Date of Patent: May 27, 1997

[54] EXPRESSION OF GENES IN TRANSGENIC PLANTS USING A CINNAMYL ALCOHOL DEHYDROGENASE GENE PROMOTER

[75] Inventor: Michael H. Walter, Filderstadt, Germany

[73] Assignee: Zeneca Limited, England

[21] Appl. No.: 347,340

[22] PCT Filed: May 27, 1993

[86] PCT No.: PCT/GB93/01098

§ 371 Date: Feb. 28, 1995

§ 102(e) Date: Feb. 28, 1995

[87] PCT Pub. No.: WO93/24638

PCT Pub. Date: Dec. 9, 1993

[51] Int. Cl.$^6$ .............................. A01H 5/00; C12N 15/11; C12N 15/82

[52] U.S. Cl. .................. 800/205; 536/23.1; 536/24.1; 435/69.1; 435/172.3; 435/320.1; 435/419; 435/414

[58] Field of Search .................. 536/23.1, 24.1; 435/69.1, 172.3, 240.4, 320.1; 800/205

[56] References Cited

FOREIGN PATENT DOCUMENTS 2005597 6/1990 Canada .

935159 3/1993 WIPO .

OTHER PUBLICATIONS

Leyva et al: "cis–Element combinations determine phenylalanine ammonia–lyase gene tissue–specific expression patterns", The Plant Cell, vol. 4, No. 3, Mar. 1992, see whole document.

O'Malley, et al: "Purification, characterization, and cloning of cinnamyl alcohol dehydrogenase in Loblolly Pine (*Pinus taeda* L.)", Plant Physiology, nol 98, No. 4, Apr. 1992, pp. 1364–1371, see the whole document.

Halpin, et al: "Purification and characterization of cinnamyl alcohol dhydrogenase from tobacco stems", Plant Physiology, vol. 98, No. 1, Jan. 1992, see the whole document.

Kim et al (1994) Plant Mol. Biol 24:105–117.

*Primary Examiner*—David T. Fox
*Assistant Examiner*—Elizabeth F. McElwain
*Attorney, Agent, or Firm*—Cushman Darby & Cushman IP Group of Pillsbury Madison & Sutro

[57] ABSTRACT

A gene promoter sequence has been isolated and characterised from the plant gene encoding the enzyme cinnamyl alcohol dehydrogenase (CAD), an enzyme which participates in the biosynthesis of lignins. The promoter may be used to control expression of exogenous genes placed under its control. Genes controlled by the CAD promoter is inducible by wounding.

5 Claims, 8 Drawing Sheets

FIG. 1A

Tobacco Genomic CAD Clone gNtCAD9 (14 kb Insert)

FIG. 2A

```
SEQ ID NO: 1
SEQUENCE TYPE: Nucleotide
SEQUENCE LENGTH: 6877
STRANDEDNESS: single
TOPOLOGY: linear
MOLECULAR TYPE: genomic ORIGINAL SOURCE ORGANISM: tobacco cv NK326
IMMEDIATE EXPERIMENTAL: tobacco genomic DNA library FEATURES: from 1 - 2765 promoter
          from 2875 - 6579 coding seqence and introns PROPERTIES: genomic DNA of cinnamyl alcohol dehydrogenase - gNtCAD9
```

```
  1  GTCGACCTGC AGGTCAACGG ATCATATATT ATGTGTCTTT ACCTATACTA TTATCACTAA
 61  ATCAATAAAT GTCTAACTGC AATGATCGTG TTAAATTGTG TATCAGAGAA TTGAGTGACT
121  GATATATAGT AGGCATTTGA AAGTTGAAAG ATGAATTTCA CACTAAACTC AGATAAGATG
181  ATTTGTGGG GTAGGCATTT GATTAAATGC AAAACCTACT CTCATGAATG TCAGTTTAAC
241  AACACAATCA ACCAAATGAA TTCTAAAAAC AAGAATTTTA CTGGGGAAAA AAACGTTTCG
301  AATAAATAAG AATATCGTAA AATTAATATT ACCAACAAA TTTGCATTGG TTATAACTTA
361  TAATCACGTG AAATGATTTG TACCAATACC TTATTTGGAT CCAAAGCCTG GCTAATTGT
421  TTCTTACCTT CTTTGCACA AGCAACCTCT TTTTAGCTTC TTCTACCTAT ATTACCTACT
```

FIG. 2B

```
 481  AACTTTTAAG AGTCCAAAAC CTAAAATAAA TCAAAAGTTT TTTTTAAAAA AAAAAAAAA
 541  AAAAAAAAAA CCTTACCTAA AACATGACGA TCTAGTGACG CATACTTCCA CCTAACCCCG
 601  GGGGACCCAA ACTGCTTGTC CAGAACAATT AATGCTTTCT TTTAGGAAGT TATCATTCAC
 661  ATAATTCATC TAGGCCTGTG ATAAAGATAA TTGGTCATTA TTGAAAAGT CGTCTCACGT
 721  AGGAAGAGAT TGCTAAACTA GAATTTGAAA TTTGAGTCCT CTGAATTTGA CGTCGAATTC
 781  ACTGCATATT TTAATTACTG AGTTCATATAT TATATATTAG TATAAATTTA ATTGATTCTC
 841  TCGTATAAAT ATAGACTTTA TGCAAAGCT ACGAGTTCGA TCAAACCCGT AAATAATATG
 901  TTACCTCCGT TTCCTAGTAG GAAGACAGAA ACAAATATCA AAAGAAAGG AAAAAACAT
 961  TTCACACTCT ACGTACCTTT CTATAATTTC AAAATAAAAG TTGGTGAAAG GGAAAATGG
1021  TTAGAGAAA AATAAGATAG GAGAACAG TTCGTAAGGA ATTTAAATT
1081  AAAATATATT AATTTGTTT TACAAGTTAT TTAAGAACTT TAGAAGACGA ATAACAACAA
1141  TGTTTTTTT CTGTTTTAGT AATTTTCATA ACATATGAAC TAAATGCTCT TTTAAAAAGT
1201  TTTTAGGGAA AAGAAAAACG AAAAATTAAA GTGGTGTAT CAAGAAAGCA AAACATATGA
1261  TCAGATTTTC CGGCATATTT ATAGGATTAT TAACGATGGT TTACTCAGTT ACAAGGTTCC
1321  CGAGAAATTA ATTTTGAAAA TATTAACAGA AAAAAGCCCA AATAAACACT TTTTCTTTA
1381  AGATTATTT ATTTAGGCCT CGTTAGTTTG CATGGAGGTT TGAATCTTAA TCATTCAGAT
1441  CTCAGATATT GACTGCGTTT CTTTTTAAGT ATAAATCTTA ATTATTCAGA TCTTAATCAT
1501  TAAATTTTTT TAAACCACTG AATGAGTCTG AAATCTGAAT AGTCTTATT GATTACGATT
1561  TATAACAGAG ACTTAATTTT ATTAAGATGT TATCATCCAT ATTCACTACT AACCACCGCC
1621  ATTATCACCT ACCACCATGC ACCATCCAAC CAATACCAAA CTCAACCACC ACCAAATTCA
1681  AACACCATCA CTAACCACCA CTATCTCACT ACCCCATAAT TATCAACTAA TCACCTCCAA
1741  CCCCACCATT ATCGATTACC ATCACCTACC AACTACTACC ATCAACCCCC CCAACCACCAT
1801  ATCAATCACA AACATCTATC CACTCACCTC GTCCTCCACG CTTCCTCGAC CATAACTACT
1861  AATCAACCAT AGCTACCATT TATTACTTGG AACCATCACC AACCGCCGCC TCCAGTCGGA
1921  ACTACCCAAT CACCACTAGT CACCACTAC ACCAACTATC ATATTATTTT TCAAAAATAT
1981  TCCATAAGCC TCACCGTCAA CCATCACTAC AATATTTAT TTGAATTTT TATTTATTAT
2041  ATTTATTATT AATAGAATAT TAAATTAATT AATATTTTAT ATCAAACAGT CTTAATCATT
2101  TTTTAGATAA TGATAAATTT TATACATTCA GATGTTGAAA ATCAAACATG TTCAAACGTT
2161  TAGTATTCAT ATATTAATAT AATATTTACA TAATCAGATG TCTATTCTGA AACAAATGAG
2221  TTAATCTTAA TACACATCTT AATATTTATT TGTCTCTTTA TCTTTAAATA AGTAGTAA
2281  GCCTTAGCTG TCTTCACATA ATTCTTTATT GCTGTGCTAT TAATGAGTAC GAATTAGTAA
2341  TTCTCTTAAC GAACAGTGAG TAGTTTGCTA ACTTTATATT CGTTTATTGT AGTATATTG
```

FIG. 2C

```
2401  TGTATTATAA GAATAAAAAA ATATTAGCA CTTATTTGGT TAGTATTAAT TTCCACGGAC
2461  ATTTTAAAG CATATTTCC AAGCTGTATC TATTTTTTTT TCCTTCCTCT CATCTCAAGA
2521  TGCAAGTGTC ATTAATTTG TACAACATGT CGATTAATAT AGTGATTACA ATTATTACCT
2581  TACTGTTCAC GTATAGGTTG GAAATATAAT ATAAGCATCT ACTCAATCCA ATTATAAAAC
2641  TTGATGTCTA TATCTTAGCT ACTGAGCAAA AAATCAACTT TTGTAAATTC TAGAAGAAAC
2701  GCCACCCAAC CTCTGTCTTC CCCTTCTTTA AACTATATAT ATGTGGTGTT ATTAACCAAA
2761  CTGTACTAAA ATAGCTCACC ACTATTCCTT TCTCTTTCCC TTGAACTGTG TTTTCGTTTT
2821  TTCTGCTCTA AAACAATAGT GTGTTCCTTC TAGATTTTAA GTTTAAAGAA CATCATGGGT
2881  GGCTGGAAG TTGAGAAAAC AACTATTGGT TGGGCTGCTA GAGACCCTTC TGGTGTACTT
2941  TCACCTTATA CCTATACTCT CAGGTACATT ACATTACTAC TTATGTTCTT TCTATAATCG
3001  TAATATCCGA ATCAGCTTAT GCTTACCCTCG ACTACTTATT TTTATCTTAT AATAACTATT
3061  CTACCAATTT TAAGATGAGT TATGAACTTT GTTTTTTGTT TTTCATGTCC AGAAACACAG
3121  GACCTGAAGA TGTGGAAGTC AAAGTTTTGT ATTGTGGGCT CTGCCACACT GATCTTCACC
3181  AAGTTAAAAA TGATCTTGGC ATGTCCAACT ACCCTCTGGT TCCTGGGTAT TTGCTCTTCC
3241  CTCTCTATTT TCCCTGTTTT TTCTCTCTCT CTATATATAT ATATAAAACA TAATTTGAGA
3301  GTTCAAGTTT TGTGGACAAA ATGAGGATCA CTATTGATCC CCTAAGGATG GAGGAAAATT
3361  GATTAATTAG AAGAGAAACA AGAGTTTGAC AGTAATTTTT TCAAGGATAA TTTAACTTGT
3421  TTTAGCATAG GTTGTTGCAG TATTCTTGAG ATTACGAATT TCATTTATGA TAAATACTTG
3481  TAAGTATATT TTAAGTGATC TGATAGCTAG AAATTCTTTA CACGCTTTTA AATATATGAA
3541  TGTTAAAATT CTCCTACAAT GGTACCCTTT GAATCTTTGT TTGATGTCAA TTTCAGTTTT
3601  TTCCTTAGCC ACTGAATAAA TCAAGAGAAA TGTAGTGGTC CTGTGCCTT TTAGTACCAA
3661  TCCACCATCC TCGGTGACTT AATAAATTTG CAACTGTTAG TTGTTAGGAT TTGATTTATT
3721  ATTCCAAATG TCTTTTTTTC CTTCCTTTAT CTCCTTTTAT ATGAGTACTA TTGAATTGTT
3781  TAATTAGGAG TTGTGGCAGA CCACGTATTT TCGTGGCCTA AATGCCAAAG CAAACATATA
3841  ATAACGTACG ACTAAGTTCA CTTCTTTCAT TGGATTTGTA AAAGTTGTTG GTGACACTTA
```

FIG. 2D

```
3901  CGTTTGTTC GAATCCAATG CTATTATTGT TAGATAAATT TTTACTTTTA GTCCCTAAAA
3961  TTATTGATAA GTTATAATTT TAATCCTTGT ACTATTGGC GAAGTACATT TAGTCTTCAA
4021  TTTAATTAAA ATTAGACATT TGATCCTGCT TCTGCTTGTG AATCTTCACA AAGTTAATCA
4081  ATTATGAATT CATGAATTAT GTTAAATTTG TGTTGTTACT CCCTATCTAA GGATACTAGA
4141  GTTCTAATTC ATAAGTAGCG GTGGTAAAAT AGATAAAAAT AATAATTATC CATTCATTTT
4201  ATCCACTAAA AAATAAATAA CCAATGAATT TAACTTTTAT ATTACAAAC CCTTAATTGA
4261  AGGGTTTCTC AAGTTTGAGA TACTAAGAAT TCTCTCAAAA GTAATCATAT TGAAGAAGTT
4321  ATGAATCATA TGTATATCCA TATTATCTGT CAATTAACTA TTTTTTATCC ATATTAAATA
4381  TAGATAAGGT TGAATATTAT ATTTATTAGA CGCCCATTTG TCACCCCTAT AATCACAATT
4441  GCAATATCCC TTTTGTTTTT TACTATGTGT TGATCCTTAT CCCTTTGTAA CTTCATATTT
4501  GTGGTGAATG ATGTAGACAT GAAGTGGTGG GAGAGTAGGA CCAGATGTGT
4561  CAAAATTCAA AGTGGGGGAC ACAGTTGGAG TTGGATTACT CGTTGGAAGT TGCAGGAACT
4621  GTGGCCCTTG CAAGAGAGAT ATAGAGCAAT ATTGCAACAA GAAGATTGG AACTGCAATG
4681  ATGTCTACAC TGATGGCAAA CCCACCCAAG GTGGTTTTGC TAAATCCATG GTTGTTGATC
4741  AAAAGTAAGT CTTTTACCCT TCCATATATA TAGAGAAGTA CCTTTCTTTA ATATTAACTT
4801  ATAGCAAGTG ACATTGTATA TAAGTTACAC CCTGTAAATT AAAGAAACTA TCAGTATAAC
4861  TTACCTGTCG TAATAGGTTG GTTGCCTTAT TTTGAGGTAA TTAGTTTTAC TTATTGTGGA
4921  CAGAGCTACA ACTATTAGA TAATAGGATG GTATAAAACA ATTTCTACAC TATCATTGTG
4981  TTTGTTCAAC TCTTTTTTAA ATCCATTGGG TATCGAATCA TGACAAATGT TACTAGGACG
5041  ATCAAGAAAT CATGTAGGGC AGCCCTGTAC ACTAAGCTCG CGCTATGCGG TCCGGGGAAA
5101  GTCGGACCAC AAAGGTATAT TGTATGTAGT CTAACCCTGC ATTTCTGCAG AGGTGCTCGA
5161  ACCCGTATCC TCTTTGGTCA CATGGTAATA ACTTAACCAG TTACGCCAAG GTTCCCCTTC
5221  AAGAAACCAT ATAATTAAAG TGGTTAATTC ACATTTCTTG AATTAAAAGA TCACAATGGA
5281  CTGAATGTTA TTTTGCCTTG TATATAGGTT TGTGGTGAAA ATTCCAGAGG GTATGGCACC
5341  AGAACAAGCA GCACCTCTAT TATGTGCTGG TATAACAGTA TACAGTCCAT TGAACCATTT
5401  TGGTTTCAAA CAGAGTGGAT TAAGAGGAG AATTTTGGGA TTAGGAGGAG TGGGACACAT
5461  GGGAGTGAAA ATAGCAAAGG CAATGGGACA TCATGTTACT GTCATTAGTT CTTCAAATAA
```

```
5521  GAAGAGACAA GAGGCATTGG AACATCTTGG TGCAGATGAT TATCTTGTCA GTTCAGACAC
5581  TGATAAAATG CAAGAGGCTT CTGATTCACT TGACTATATT ATTGATACTG TCCCTGTTGG
5641  CCATCCTCTT GAACCTTATC TTTCTTTGCT TAAAATTGAT GGCAAACTTA TCTTGATGGG
5701  AGTTATCAAC ACCCCCTTGC AATTTATCTC CCCCATGGTT ATGCTCGGTA AGTCATTTAA
5761  CTTATTTACG CTGACAGTGT AACACGTTCG GACGAAATGC ATTATTACAA CAAGTTAAAA
5821  TTGGTTTCTA ACAATATATC GTGTTAGTAC TTGCTCTAAA AAGTCGATTG AAAATTTAAA
5881  CGTTGAATTT GTCTATATAT GAAAAAAGAT AGAACAAAAG GATTGGAAGA GTGGTCATTT
5941  TAGTCAATGA AAGCCATGAT TGTTTGAAAT ATGCAGGTGC CATTGGTCTA TTTTGCGGC
6001  ATAATAAATGT TATGAGCAGA ATTAATATAT AGACAAATTC TAGGCTTGTA GGGTTGTGTT
6061  ATTTAAGGAA CCATGTCTGC AATAATGGAC TGCAATAACA ACAGAGACCA TACACGTATT
6121  AAAGCCAATG TATTTGATTA ACATTTGTTT AATGCAACCT CTTATTACTA TTATGTTTTA
6181  AGATTTTTA AGCACAGACA GTGTGTAAGT TTTTTATAC CATCAAGCAA AGTTGATATA
6241  TTCCGAAAAG AAAAGTTGAT GTACAATAAT AGATAACATI TCATTAGTGT GGTATGGTAA
6301  TTTGAAAGTA GTACTCGGTA TAATTTTCA TTTTACATTG TCGGCGTATA TAACTTTTAG
6361  ACTTTATTAT TATGATCAGG GAGAAAGAGC ATCACAGGAA GCTTTATTGG TAGCATGAAG
6421  GAAACAGAGG AAATGCTAGA TTTCTGCAAA GAGAAAGGTG TGACTTCACA GATTGAGATA
6481  GTGAAAATGG ATTATATCAA CACTGCAATG GAGAGGTTGG AGAAAAATGA TGTGAGGTAC
6541  AGATTGTGG TTGATGTTAT TGGAAGCAAG CTTGACCAGT AATTATATTA CACAAGAAAA
6601  ACAACATGGA ATGGTTCACT ATTATACAAG GCTGTGAGAA TACTAAACTT TGATGTCGTC
6661  TTTTGTATCC ATGGTTCTT TTTGCCACCT GTATTTTCTT ATTTGGTGAT CGAGAGTGAC
6721  GTTTATGTAT TATTTCTTT CTTCAAAACA ATTAATGTA TGAATTTGGA TGTTGGTGAC
6781  GATTTGAAA TATACCAACC AAAACTTTGT TGGTACGTG AAGCTATCTC CACTTCTCGT
6841  GACTAGGGTG TCGATCCATC TTTAAATCGA TTAACCG  6877
```

EXPRESSION OF GENES IN TRANSGENIC PLANTS USING A CINNAMYL ALCOHOL DEHYDROGENASE GENE PROMOTER

BACKGROUND OF THE INVENTION

The present invention relates to the regulation of gene expression in transgenic plants. In particular it is concerned with the isolation and use of DNA sequences which control the expression of genes in lignifying tissues and in response to pathogen attack.

The ability to isolate and manipulate plant genes has opened the way to gain understanding about the mechanisms involved in the regulation of plant gene expression. This knowledge is important for the exploitation of genetic engineering techniques to practical problems such as the expression of genes in genetically manipulated crop plants exhibiting improved quality and production characteristics.

Many examples have been reported in the literature of plant DNA sequences which have been used to drive the expression of foreign genes in plants. In most instances the regions immediately 5' to the coding regions of genes have been used in gene constructs. These regions are referred to as promoter sequences. They may be derived from plant DNA; or from other sources, e.g., viruses. It has been demonstrated that sequences up to 500–1000 bases in most instances are sufficient to allow for the regulated expression of foreign genes. The provide a promoter sequence suitable for the control of foreign gene expression in plants.

SUMMARY OF THE INVENTION

According to the present invention there is provided a DNA construct for use in transforming plant cells which comprises an exogenous coding sequence under the control of upstream promoter and downstream terminator sequences, characterised in that the upstream promoter is or has functional homology to a promoter of a gene of the lignin biosynthesis pathway.

Thus, the present invention comprises the use of the promoter(s) of the cinnamyl alcohol dehydrogenase or other genes involved in the lignin biosynthesis pathway to control the expression of novel and exogenous proteins and genes in these tissues.

Preferably, the promoter is the CAD promoter.

The clone gNtCAD9-6.3SH contains the promoter fragment of this gene. This clone has been deposited at the National Collections of Industrial and Marine Bacteria (NCIB), at 23 St. Machar Drive, Aberdeen AB2 1RY, Scotland, on 2nd Apr. 1992 under the reference NCIB Number 40499.

We further provide novel plant cells, and plants transformed with constructs according to the present invention. We illustrate the invention hereinafter using tobacco as a model plant species.

The constructs can be used in the expression of exogenous genes and proteins in vascular tissues, particularly but not exclusively, such as poplar, eucalyptus, pine, and other woody plants as well as forages such as festuca, alfalfa, maize, sorghum, penesitum, amongst others.

Not only will this promoter be expressed in types of regulation exemplified include tissue-specificity, regulation by external factors such as light, heat treatment, chemicals, hormones, and developmental regulation. However, it has also been shown that sequences much longer than 1 kb may have useful features which permit high levels of gene expression in transgenic plants.

These experiments have largely been carried out using gene fusions between the promoter sequences and foreign structural genes such as bacterial genes, etc. This has led to the identification of useful promoter sequences.

In the work leading to the present invention we have identified a gene which expresses an enzyme involved in biosynthesis of lignin in vascular plants. We have shown that this gene encodes cimmamyl alcohol dehydrogenase (CAD) which is one of the enzymes specific to the lignin branch pathway of phenylpropanoid metabolism. The gene in question is encoded by the cDNA clone pTCAD19 among others which are the subject of our published copending International Patent Application Number WO 93/05159.

The enzyme encoded by the CAD gene catalyses the oxidation of cinnamyl aldehydes to cinnamyl alcohols which are the direct precursors of the lignin polymer. We have isolated the gene encoding this enzyme from tobacco.

We have shown that CAD mRNA is expressed throughout plant development with the highest levels found in lignifying tissues. In these tissues the CAD enzyme can be found in high concentration in the xylem of plants.

An object of the present invention is to modified plants in a given tissue but it will also be induced in response to environmental and endogenous signals such as wounding, infection, ethylene production and others.

Promoters for use in the invention may be derived from genes such as methyl transferase, and cinnamyl CoA reductase. Such promoters may be isolated from genomic libraries by the use of cDNA probes, as has been done in the case of CAD. We particularly prefer to use the promoter of the CAD gene.

The downstream (3') terminator sequences may also be derived from the CAD gene or they may be derived from other genes. Many possibilities are available from the literature: the selection of the terminator being of rather lesser importance.

By the term 'exogenous coding sequence' we mean a sequence of DNA, other than that which follows the promoter region in the natural CAD gene, that is adapted to be transcribed into functional RNA under the action of plant cell enzymes such as RNA polymerase. Functional RNA is RNA which affects the biochemistry of the cell: it may for example be mRNA which is translated into protein by ribosomes; or antisense RNA which inhibits the translation of mRNA complementary (or otherwise related) to it into protein. In principle any exogenous coding sequence may be used in the present invention.

Where the exogenous coding sequence codes for mRNA for a protein, this protein may be of bacterial origin (such as enzymes involved in cell wall modification and cell wall metabolism), of eukaryotic origin (such as pharmaceutically active polypeptides) or of plant origin (such as enzymes involved in the synthesis of phenolic compounds, ethylene synthesis, sugar metabolism, cell wall metabolism,), or genes or parts thereof in sense and antisense orientation.

A wide variety of exogenous coding sequences is known from the literature, and the present invention is applicable to these as well as many others yet to be reported. As well as functional mRNA, the exogenous gene may code for RNA that interferes with the function of any kind of mRNA produced by the plant cell: for example, antisense RNA complementary to mRNA for genes such as stilbene synthesis, phytoalexin synthesis and flavour and pigment synthesis.

Of particular interest is the ability of the CAD gene promoter to respond to exogenous stimuli.

The construction of vectors and constructs of the present invention will be described in more detail in the Examples below. For convenience it will be generally found suitable to use promoter sequences (upstream—i.e. 5'—of the coding sequence of the gene) of between 100 and 2000 bases in length.

A particularly preferred embodiment of the invention is a promoter for use in the expression of exogenous genes in plants, comprising the promoter of cinnamyl alcohol dehydrogenase.

More particularly the promoter of the invention comprises the nucleotide sequence shown in FIGS. 2A–2E, taken together (SEQ ID NO:1). The invention includes modifications or the use of only parts of the said sequence which, while retaining sufficient homology to the said sequence in order to maintain functionality, enhance or alter its tissue-specificity or response to external stimuli.

The invention further provides a recombinant gene construct comprising, in sequence, a promoter according to this invention, a coding region and a gene terminator.

The invention further comprises a recombinant plant genome containing the said construct.

Plant cells may be transformed with constructs of the invention according to a variety of known methods (Agrobacterium Ti plasmids, electroporation, microinjection, microprojectile bombardment, etc). The transformed cells may then be regenerated into whole plants in which the new nuclear material is stably incorporated into the genome. Both transformed monocot and dicot plants may be obtained in this way. The transformation and regeneration methods employed are not particularly germane to this invention and may simply be selected from those available from the literature.

Examples of genetically modified plants according to the present invention include tomatoes, fruits such as mangoes, peaches, apples, pears, strawberries, bananas and melons; and field crops such as maize (corn), sunflowers, sugarbeet, canola, and small grained cereals such as wheat, barley and rice, ornamental plants such carnations, petunias, roses, chrysanthemums etc.

Plants produced by the process of the invention may contain more than one recombinant construct. As well as one or more constructs containing the cinnamyl alcohol dehydrogenase promoter, they may contain a wide variety of other recombinant constructs, for example constructs having different effects on plant development, structure and defense. In particular, constructs which affect lignin structure, composition and quality and quantity, cellulose and hemicellulose structure and amount, and plant defense genes are included in this invention.

Of particular interest is the ability of the CAD gene promoter to respond to exogenous stimuli. Thus, a further aspect of the present invention is a process of activating exogenous coding sequences in plants under the control of the CAD promoter which comprises the application of exogenous stimuli such as viruses, fungi and bacteria, as well as ethylene and other chemicals. This may find particular use when the expression of novel characters in the plant may need to be controlled exogenously.

We now describe the isolation of genomic clones from a tobacco genomic library encoding the cinnamyl alcohol dehydrogenase gene and related sequences. Genomic clones representing one of the closely related CAD genes found in tobacco have been isolated and characterised by DNA sequence analysis. The clone gTCAD9 represents the whole of the gene with exon sequence identical to the clone pTCAD14 with only two mismatches. The genomic clones described in the Examples cover all of the coding region and the complete transcriptional initiation region of the CAD gene. The subclone gNTCAD9-6.3SH contains approximately 2800 bp of the promoter fragment of this gene.

BRIEF DESCRIPTION OF THE DRAWINGS

The invention will be further described with reference to the following drawings, in which:

FIGS. 2A–2E, taken together, show the nucleotide sequence of the CAD promoter and the CAD structural gene, most of which is contained in the 6.4 kb SalI-HindIII fragment of gNTCAD9 (SEQ ID NO:1).

DESCRIPTION OF THE PREFERRED EMBODIMENTS

EXAMPLE 1

1.1 Isolation of CAD genes

A tobacco genomic library (*N.tabacum* cv NK 326) was purchased from Clontech. This library contains MboI partially digested genomic DNA cloned into lambda EMBL3. The library was screened with the pTCAD14 cDNA insert and positive phages were purified by four successive cycles of plaque purification. Four positive clones were isolated.

Figure 1A:
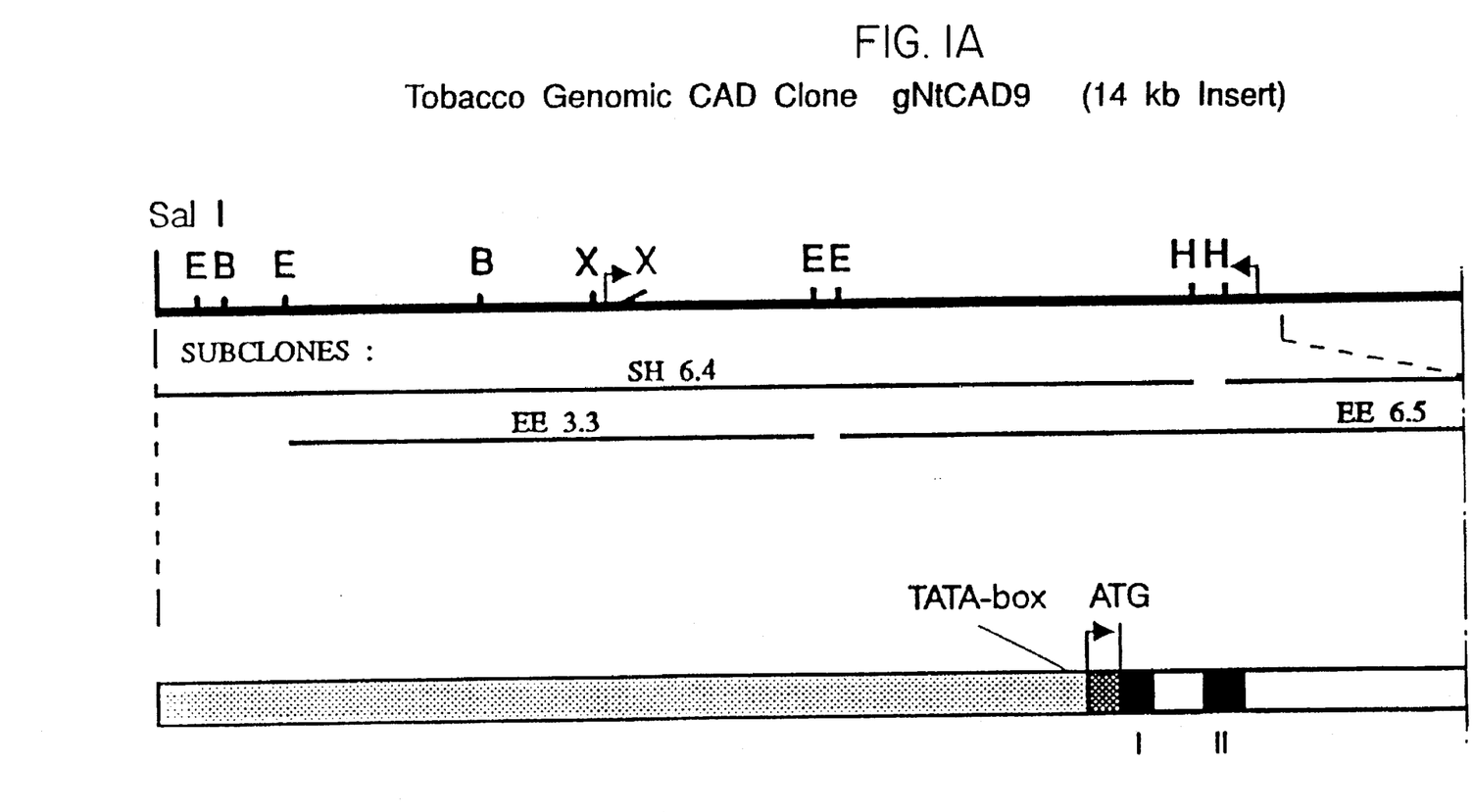
FIGS. 1A and 1B show a restriction map of gNtCAD9 and a diagram of the structure of the CAD gene.
Figure 1B:
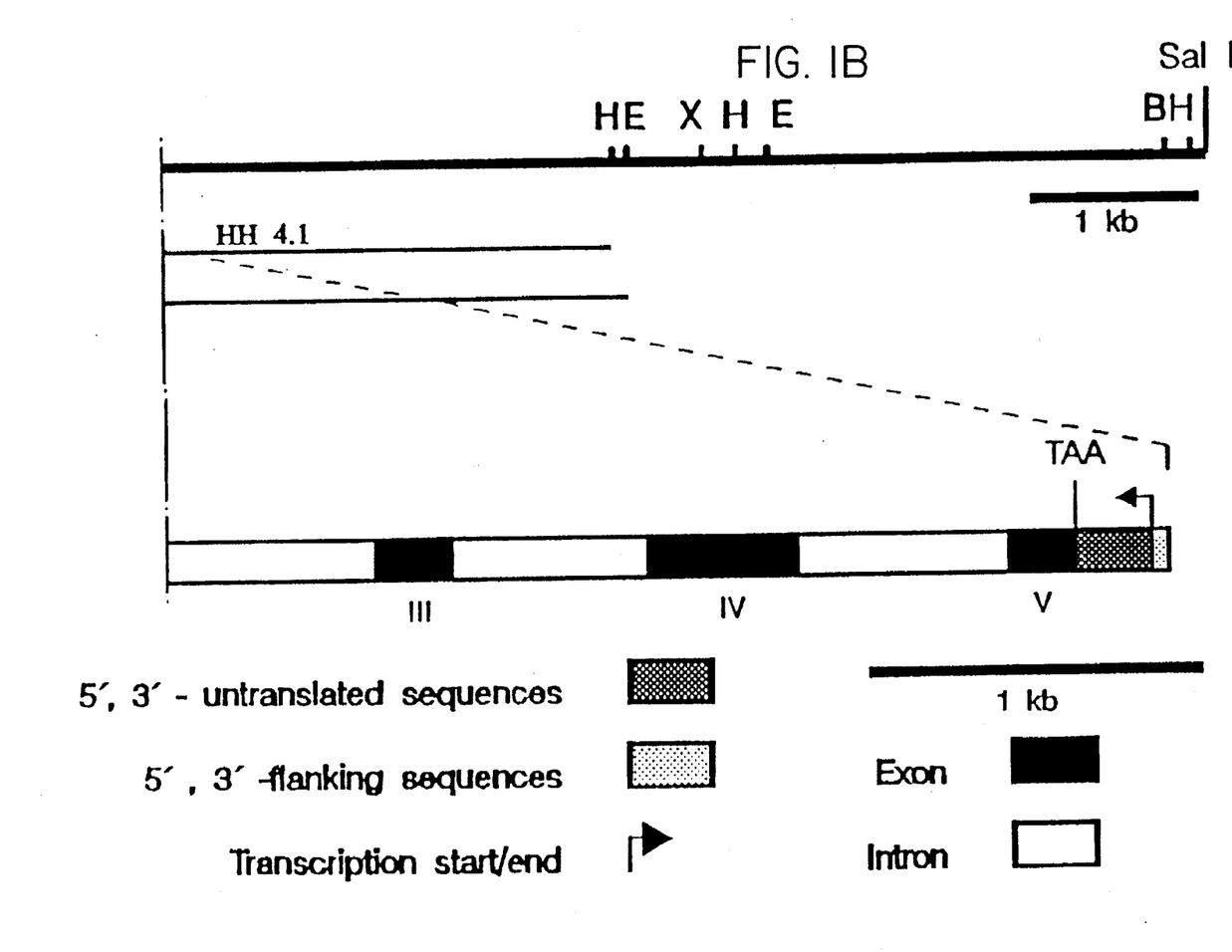

Restriction fragment mapping and DNA sequence analysis of these clones indicated that all 4 clones are overlapping clones of the CAD gene and are related. Only clones 2 and 9 contain promoter sequences and only clone 9 was characterised in detail. A restriction map of this clone is shown in FIG. 1.

1.2 Characterisation of the CAD gene promoter sequence

Figure 2A:
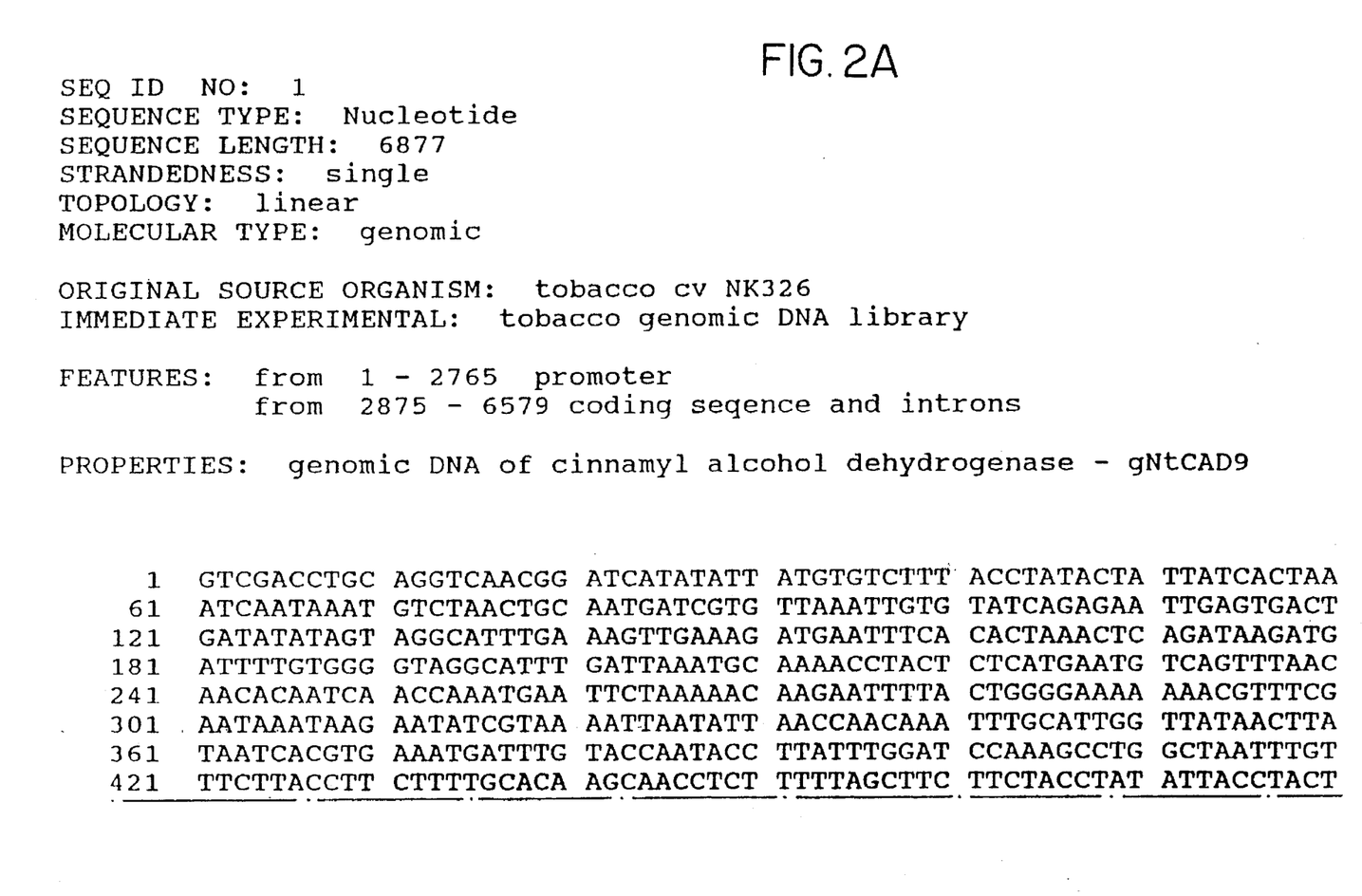

A 6.4 kb SalI-HindIII fragment was isolated from gNTCAD9 and the nucleotide sequence covering 2765 bp of the 5'-flanking (promoter) sequences and most of the coding sequences has been determined (FIG. 2). Primer extension experiments place the transcription start point at nucleotide position 2766.

Full sequence data of about 6.8 kb have been obtained of a tobacco CAD gene contained on clone gNtCAD9. The following are thereby confirmed:

(A) Transcription start site mapped to position 2766 from the upstream Sal 1 border, now designated position +1, placing the ATG start codon at +110

(B) Position and exact size of the four introns: (1) at +198, size 149 bp; (11) at +312, size 1290 bp; (111) at +540, size 563 bp; (IV) at 980, size 632 bp. The intron position and sizes differ from the ones in ADH genes.

(C) Three nucleotide mismatches to cDNA cNtCAD14, which are all silent with respect to the deduced protein. They can be ascribed to cultivar differences between cDNA and genomic library.

1.3 Fusion of CAD promoter to the GUS reporter gene

A XbaI site at position +84 was used to isolate the CAD promoter from gNtCAD9 and create a transcriptional fusion of 2849 bp of promoter and leader sequences to the GUS reporter gene in pBI 101.4. The promoter fragment was isolated after partial XbaI digest due to a second XbaI site in the promoter. Correct fusion and fusion borders were confirmed by restriction analysis and DNA sequencing.

1.4 Construction of plant transformation vector—pCAD-gus

Figure 3:
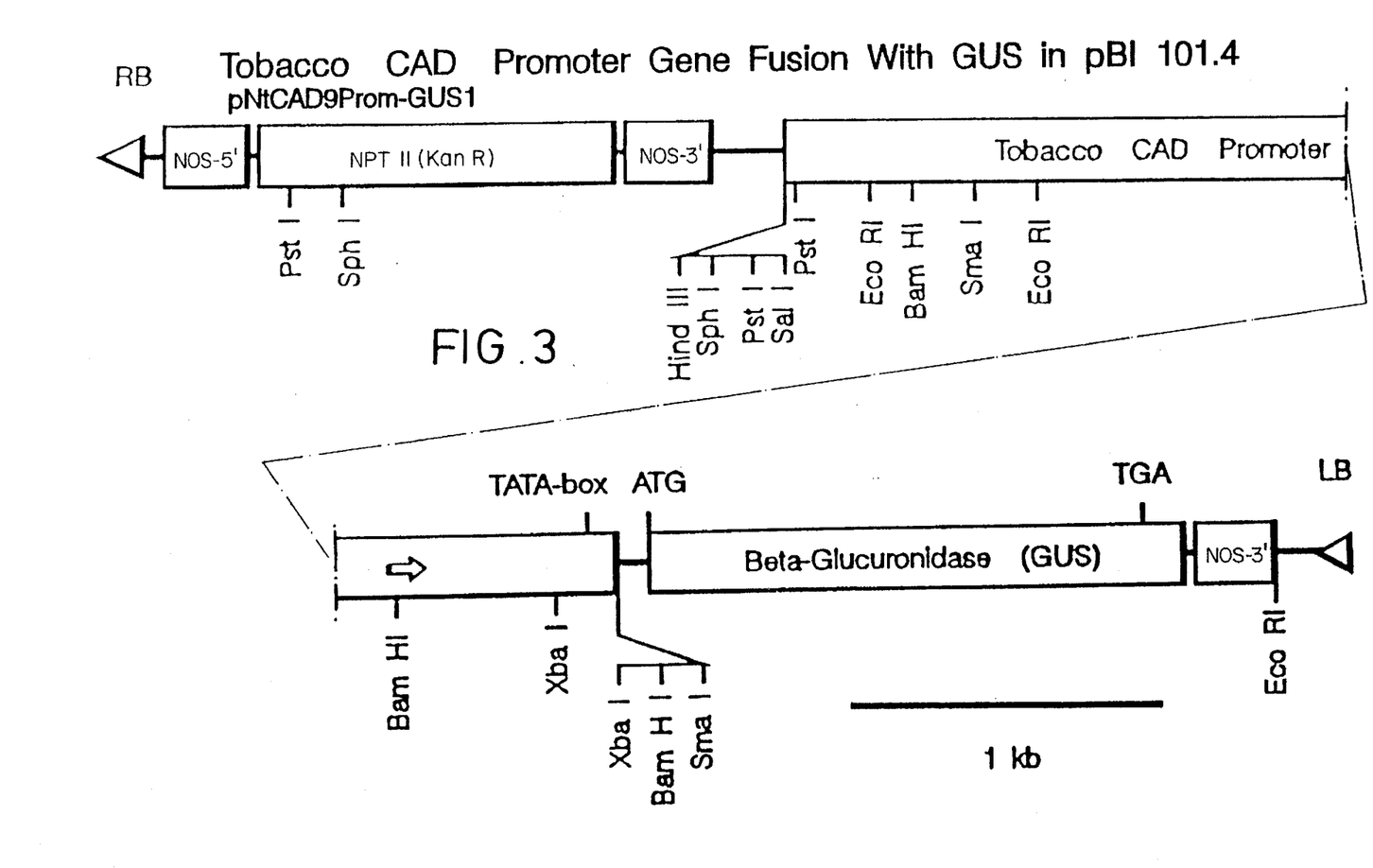
FIG. 3 outlines a scheme for construction of the plant transformation vector pNtCAD9Prom-GUS1.

The plasmid subclone gNtCAD9-6.4SH containing the 6.4 kb SalI-HindIII fragment was digested with SalI and partially digested with XbaI to recover a 2853 bp SalI-XbaI fragment, which contains all of the available CAD promoter sequence and 87 bp of leader sequence. This promoter fragment was inserted into the appropriately cut polylinker of the promoterless GUS cassette of the binary plant transformation vector pBI101.4 in the 5'-3' orientation (FIG. 3). The correct insertion has been confirmed by DNA sequencing of the fusion borders.

EXAMPLE 2

Generation of transformed plants

The vector pNtCAD9Prom-GUS1 (from Example 1.4) is transferred to *Agrobacterium tumefaciens* LBA4404 (a micro-organism widely available to plant biotechnologists) and was used to transform tobacco plants. The fusion construct was introduced into *Agrobacterium tumefaciens* LBA 4404. Tobacco cv. SR1 leaf discs were transformed via cocultivation with Agrobacteria harbouring the construct. Transgenic shoots were rooted and further propagated by standard procedures. Transformation of tobacco leaf disks follows established methods. Transformed plants were identified by their ability to grow on media containing the antibiotic kanamycin. Plants were regenerated and grown to maturity.

The tissue-specific and developmental expression and expression in response to external stimuli of the β-glucuronidase (GUS) gene as determined by the CAD gene promoter is demonstrated by analysis of stems, roots, leaves, seeds, flowers, pollen and in response to wounding and ethylene treatment for GUS enzyme activity.

EXAMPLE 3

Expression of CAD promoter—GUS fusion in transgenic tobacco

From 20 transformants regenerated 11 have been analysed in some detail. Quantitatively (fluorometric analysis), GUS activity is highest in roots followed by stems and leaves. Histochemical staining by X-gluc indicates strong expression in the vascular system of stems and leaves preferentially in the developing xylem, where lignification is known to occur. No activity was detectable in pith or epidermal tissue. However, leaf and stem hairs ((trichomes)) exhibit considerable GUS expression in certain stages of their development. One example is the region around axillary buds, where strong staining of trichomes was observed. Upon wounding of stems a local induction of promoter activity was seen during the development of a wound plug but only 10–20 days after wounding.

I claim:

1. A DNA construct for use in transforming plant cells which comprises an exogenous coding sequence under the control of upstream promoter and downstream terminator sequences, characterised in that the upstream promoter is a promoter of a cinnamyl alcohol dehydrogenase gene having a nucleotide sequence comprising the first 2765 nucleotides of SEQ ID NO:1.

2. An isolated cinnamyl alcohol dehydrogenase gene promoter, having the nucleotide sequence comprising the first 2765 nucleotides of SEQ ID NO:1.

3. The cinnamyl alcohol dehydrogenase gene promoter which is present in the clone designated gNtCAD9-6.3SH which has been deposited at the National Collections of Industrial and Marine Bacteria (NCIB), at 23 St. Machar Drive, Aberdeen AB2 1RY, Scotland, on 2nd Apr. 1992 under the reference NCIB Number 40499.

4. Plants and plant cells transformed with a construct claimed in claim 1.

5. A recombinant plant genome comprising a cinnamyl alcohol dehydrogenase gene promoter having a nucleotide sequence comprising the first 2765 nucleotides of SEQ ID NO:1, said promoter being located to drive expression of an exogenous gene.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 6877 base pairs
        ( B ) TYPE: nucleic acid
        ( C ) STRANDEDNESS: single
        ( D ) TOPOLOGY: linear     ( i i ) MOLECULE TYPE: DNA (genomic)

( v i ) ORIGINAL SOURCE:
        ( A ) ORGANISM: Nicotiana tabacum     ( x i ) SEQUENCE DESCRIPTION: SEQ ID NO:1:

```
GTCGACCTGC  AGGTCAACGG  ATCATATATT  ATGTGTCTTT  ACCTATACTA  TTATCACTAA       60

ATCAATAAAT  GTCTAACTGC  AATGATCGTG  TTAAATTGTG  TATCAGAGAA  TTGAGTGACT      120

GATATATAGT  AGGCATTTGA  AAGTTGAAAG  ATGAATTTCA  CACTAAACTC  AGATAAGATG      180

ATTTGTGGG   GTAGGCATTT  GATTAAATGC  AAAACCTACT  CTCATGAATG  TCAGTTTAAC      240

AACACAATCA  ACCAAATGAA  TTCTAAAAAC  AAGAATTTTA  CTGGGGAAAA  AAACGTTTCG      300

AATAAATAAG  AATATCGTAA  AATTAATATT  AACCAACAAA  TTTGCATTGG  TTATAACTTA      360

TAATCACGTG  AAATGATTTG  TACCAATACC  TTATTTGGAT  CCAAAGCCTG  GCTAATTTGT      420

TTCTTACCTT  CTTTTGCACA  AGCAACCTCT  TTTTAGCTTC  TTCTACCTAT  ATTACCTACT      480

AACTTTTAAG  AGTCCAAAAC  CTAAATAAA   TCAAAAGTTT  TTTTAAAAA   AAAAAAAAA       540

AAAAAAAAA   CCTTACCTAA  AACATGACGA  TCTAGTGACG  CATACTTCCA  CCTAACCCCG      600

GGGGACCCAA  ACTGCTTGTC  CAGAACAATT  AATGCTTTCT  TTTAGGAAGT  TATCATTCAC      660
```

| | | | | | |
|---|---|---|---|---|---|
| ATAATTCATC | TAGGCCTGTG | ATAAAGATAA | TTGGTCATTA | TTGGAAAAGT | CGTCTCACGT | 720 |
| AGGAAGAGAT | TGCTAAACTA | GAATTTGAAA | TTTGAGTCCT | CTGAATTTGA | CGTCGAATTC | 780 |
| ACTGCATATT | TTAATTACTG | AGTTCATAAT | TATATATTAG | TATAAATTTA | ATTGATTCTC | 840 |
| TCGTATAAAT | ATAGACTTTA | TGCAAAAGCT | ACGAGTTCGA | TCAAACCCGT | AAATAATATG | 900 |
| TTACCTCCGT | TTCCTAGTAG | GAAGACAGAA | ACAAATATCA | AAAGAAAGG | AAAAAAACAT | 960 |
| TTCACACTCT | ACGTACCTTT | CTATAATTTC | AAAATAAAAG | TTGGTGAAAG | GGAAAAATGG | 1020 |
| TTAGAGGAAA | AATAAGATAG | GAGAGAACAG | AAACTATGTA | TTCGTAAGGA | ATTTAAAATT | 1080 |
| AAAATATATT | AATTTGTTT | TACAAGTTAT | TTAAGAACTT | TAGAAGACGA | ATAACAACAA | 1140 |
| TGTTTTTTTT | CTGTTTTAGT | AATTTCATA | ACATATGAAC | TAAATGCTCT | TTTAAAAGT | 1200 |
| TTTAGGGAA | AAGAAAAACG | AAAATTAAA | GTGGTTGTAT | CAAGAAAGCA | AACATATGA | 1260 |
| TCAGATTTTC | CGGCATATTT | ATAGGATTAT | TAACGATGGT | TTACTCAGTT | ACAAGGTTCC | 1320 |
| CGAGAAATTA | ATTTTGAAAA | TATTAACAGA | AAAAAGCCCA | ATAAACACT | TTTTCTTTA | 1380 |
| AGATTTATTT | ATTTAGGCCT | CGTTAGTTTG | CATGGAGGTT | TGAATCTTAA | TCATTCAGAT | 1440 |
| CTCAGATATT | GACTGCGTTT | CTTTTAAGT | ATAAATCTTA | ATTATTCAGA | TCTTAATCAT | 1500 |
| TAAATTTTT | TAAACCACTG | AATGAGTCTG | AAATCTGAAT | AGGTCTTATT | GATTACGATT | 1560 |
| TATAACAGAG | ACTTAATTTT | ATTAAGATGT | TATCATCCAT | ATTCACTACT | AACCACCGCC | 1620 |
| ATTATCACCT | ACCACCATGC | ACCATCCAAC | CAATACCAAA | CTCAACCACC | ACCAAATTCA | 1680 |
| AACACCATCA | CTAACCACCA | CTATCTCACT | GCTATCATTA | TCGACTACCA | TCACCTCCAA | 1740 |
| CCCCACCATT | ATCGATTACC | ATCACCCACC | ACCCCATAAT | TATCAACTAA | TACCACTACC | 1800 |
| ATCAATCACA | AACATCTATC | CACTCACCTC | AACTACTACC | ATCAACCCCC | CCACCACCAT | 1860 |
| AATCAACCAT | AGCTACCATT | GTCCTCCACG | CCACCATCAC | CTTCCTCGAC | CATAACTACT | 1920 |
| ACTACCCAAT | CACCACTAGT | TATTACTTGG | AACCATCACC | AACCGCCGCC | TCCAGTCGGA | 1980 |
| TCCATAAGCC | TCACCGTCAA | CCATCACTAC | ACCAACTATC | ATATTATTTT | TCAAAAATAT | 2040 |
| ATTTATTATT | AATAGAATAT | TAAATTAATT | AATATTTTAT | TTGAATTTTT | TATTTATTAT | 2100 |
| TTTTAGATAA | TGATAAATTT | TATACATTCA | GATGTTGAAA | ATCAAACAGT | CTTAATCATT | 2160 |
| TAGTATTCAT | ATATTAATAT | ATATCTTAAA | TAATCAGATG | TCTATTCTGA | TTCAAACGTT | 2220 |
| TTAATCTTAA | TACACATCTT | AATATTTACA | TGTCTCTTTA | TCTTTAAATA | AACAAATGAG | 2280 |
| GCCTTAGCTG | TCTTCACATA | ATTCTTTATT | GCTGTGCTAT | TAATGAGTAC | GAATTAGTAA | 2340 |
| TTCTCTTAAC | GAACAGTGAG | TAGTTTGCTA | ACTTTATATT | CGTTATTGT | ACGTATATTG | 2400 |
| TGTATTATAA | GAATAAAAAA | ATATTTAGCA | CTTATTGGT | TAGTATTAAT | TTCCACGGAC | 2460 |
| ATTTTTAAAG | CATATTTTCC | AAGCTGTATC | TATTTTTTTT | TCCTTCCTCT | CATCTCAAGA | 2520 |
| TGCAAGTGTC | ATTTAATTTG | TACAACATGT | CGATTAATAT | AGTGATTACA | ATTATTACCT | 2580 |
| TACTGTTCAC | GTATAGGTTG | GAAATATAAT | ATAAGCATCT | ACTCAATCCA | ATTATAAAAC | 2640 |
| TTGATGTCTA | TATCTTAGCT | ACTGAGCAAA | AAATCAACTT | TTGTAAATTC | TAGAAGAAAC | 2700 |
| GCCACCCAAC | CTCTGTCTTC | CCCTTCTTTA | AACTATATAT | ATGTGGTGTT | ATTAACCAAA | 2760 |
| CTGTACTAAA | ATAGCTCACC | ACTATTCCTT | TCTCTTTCCC | TTGAACTGTG | TTTTCGTTTT | 2820 |
| TTCTGCTCTA | AAACAATAGT | GTGTTCCTTC | TAGATTTTAA | GTTAAAGAA | CATCATGGGT | 2880 |
| GGCTTGGAAG | TTGAGAAAAC | AACTATTGGT | TGGGCTGCTA | GAGACCCTTC | TGGTGTACTT | 2940 |
| TCACCTTATA | CCTATACTCT | CAGGTACATT | ACATTACTAC | TTATGTTCTT | TCTATAATCG | 3000 |
| TAATATCCGA | ATCAGCTTAT | GCTTACCTCG | ACTACTTATT | TTTATCTTAT | AATAACTATT | 3060 |

| | | | | | | |
|---|---|---|---|---|---|---|
| CTACCAATTT | TAAGATGAGT | TATGAACTTT | GTTTTTGTT | TTTCATGTCC | AGAAACACAG | 3120 |
| GACCTGAAGA | TGTGGAAGTC | AAAGTTTGT | ATTGTGGGCT | CTGCCACACT | GATCTTCACC | 3180 |
| AAGTTAAAAA | TGATCTTGGC | ATGTCCAACT | ACCCTCTGGT | TCCTGGGTAT | TTGCTCTTCC | 3240 |
| CTCTCTATTT | TCCCTGTTTT | TTCTCTCTCT | CTATATATAT | ATATAAAACA | TAATTTGAGA | 3300 |
| GTTCAAGTTT | TGTGGACAAA | ATGAGGATCA | CTATTGATCC | CCTAAGGATG | GAGGAAAATT | 3360 |
| GATTAATTAG | AAGAGAAACA | AGAGTTTGAC | AGTAATTTTT | TCAAGGATAA | TTTAACTTGT | 3420 |
| TTTAGCATAG | GTTGTTGCAG | TATTCTTGAG | ATTACGAATT | TCATTTATGA | TAAATACTTG | 3480 |
| TAAGTATATT | TTAAGTGATC | TGATAGCTAG | AAATTCTTTA | CACGCTTTTA | AATATATGAA | 3540 |
| TGTTAAAATT | CTCCTACAAT | GGTACCCTTT | GAATCTTTGT | TTGATGTCAA | TTTCAGTTTT | 3600 |
| TTCCTTAGCC | ACTGAATAAA | TCAAGAGAAA | TGTAGTGGTC | CTTGTGCCTT | TTAGTACCAA | 3660 |
| TCCACCATCC | TCGGTGACTT | AATAAATTTG | CAACTGTTAG | TTGTTAGGAT | TTGATTTATT | 3720 |
| ATTCCAAATG | TCTTTTTTTC | CTTCCTTTAT | TAAACGAATG | ATGAGTACTA | TTGAATTGTT | 3780 |
| TAATTAGGAG | TTGTGGCAGA | CCACGTATTT | TCGTGGCCTA | AATGCCAAAG | CAAACATATA | 3840 |
| ATAACGTACG | ACTAAGTTCA | CTTCTTTCAT | TGGATTTGTA | AAAGTTGTTG | GTGACACTTA | 3900 |
| CGTTTTGTTC | GAATCCAATG | CTATTATTGT | TAGATAAATT | TTTACTTTTA | GTCCCTAAAA | 3960 |
| TTATTGATAA | GTTATAATTT | TAATCCTTGT | ACTATTGGC | GAAGTACATT | TAGTCTTCAA | 4020 |
| TTTAATTAAA | ATTAGACATT | TGATCCTGCT | TCTGCTTGTG | AATCTTCACA | AAGTTAATCA | 4080 |
| ATTATGAATT | CATGAATTAT | GTTAAATTTG | TGTTGTTACT | CCCTATCTAA | GGATACTAGA | 4140 |
| GTTCTAATTC | ATAAGTAGCG | GTGGTAAAAT | AGATAAAAAT | AATAATTATC | CATTCATTTT | 4200 |
| ATCCACTAAA | AAATAAATAA | CCAATGAATT | TAACTTTTAT | ATTTACAAAC | CCTTAATTGA | 4260 |
| AGGGTTTCTC | AAGTTTGAGA | TACTAAGAAT | TCTCTCAAAA | GTAATCATAT | TGAAGAAGTT | 4320 |
| ATGAATCATA | TGTATATCCA | TATTATCTGT | CAATTAACTA | TTTTTATCC | ATATTAAATA | 4380 |
| TAGATAAGGT | TGAATATTAT | ATTTATTAGA | CGCCCATTTG | TCACCCCTAT | AATCACAATT | 4440 |
| GCAATATCCC | TTTTGTTTTT | TACTATGTGT | TGATCCTTAT | CCCTTTGTAA | CTTCATATTT | 4500 |
| GTGGTGAATG | ATGTAGACAT | GAAGTGGTGG | GAGAAGTGGT | GGAGGTAGGA | CCAGATGTGT | 4560 |
| CAAAATTCAA | AGTGGGGGAC | ACAGTTGGAG | TTGGATTACT | CGTTGGAAGT | TGCAGGAACT | 4620 |
| GTGGCCCTTG | CAAGAGAGAT | ATAGAGCAAT | ATTGCAACAA | GAAGATTTGG | AACTGCAATG | 4680 |
| ATGTCTACAC | TGATGGCAAA | CCCACCCAAG | GTGGTTTTGC | TAAATCCATG | GTTGTTGATC | 4740 |
| AAAAGTAAGT | CTTTTACCCT | TCCATATATA | TAGAGAAGTA | CCTTTCTTTA | ATATTAACTT | 4800 |
| ATAGCAAGTG | ACATTGTATA | TAAGTTACAC | CCTGTAAATT | AAAGAAACTA | TCAGTATAAC | 4860 |
| TTACCTGTCG | TAATAGGTTG | GTTGCCTTAT | TTTGAGGTAA | TTAGTTTTAC | TTATTGTGGA | 4920 |
| CAGAGCTACA | ACTATTTAGA | TAATAGGATG | GTATAAAACA | ATTTCTACAC | TATCATTGTG | 4980 |
| TTTGTTCAAC | TCTTTTTTAA | ATCCATTGGG | TATCGAATCA | TGACAAATGT | TACTAGGACG | 5040 |
| ATCAAGAAAT | CATGTAGGGC | AGCCCTGTAC | ACTAAGCTCG | CGCTATGCGG | TCCGGGGAAA | 5100 |
| GTCGGACCAC | AAAGGTATAT | TGTATGTAGT | CTAACCCTGC | ATTTCTGCAG | AGGTGCTCGA | 5160 |
| ACCCGTATCC | TCTTTGGTCA | CATGGTAATA | ACTTAACCAG | TTACGCCAAG | GTTCCCCTTC | 5220 |
| AAGAAACCAT | ATAATTAAAG | TGGTTAATTC | ACATTTCTTG | AATTAAAAGA | TCACAATGGA | 5280 |
| CTGAATGTTA | TTTTGCCTTG | TATATAGGTT | TGTGGTGAAA | ATTCCAGAGG | GTATGGCACC | 5340 |
| AGAACAAGCA | GCACCTCTAT | TATGTGCTGG | TATAACAGTA | TACAGTCCAT | TGAACCATTT | 5400 |
| TGGTTTCAAA | CAGAGTGGAT | TAAGAGGAGG | AATTTTGGGA | TTAGGAGGAG | TGGGACACAT | 5460 |

| | | | | | | |
|---|---|---|---|---|---|---|
| GGGAGTGAAA | ATAGCAAAGG | CAATGGGACA | TCATGTTACT | GTCATTAGTT | CTTCAAATAA | 5520 |
| GAAGAGACAA | GAGGCATTGG | AACATCTTGG | TGCAGATGAT | TATCTTGTCA | GTTCAGACAC | 5580 |
| TGATAAAATG | CAAGAGGCTT | CTGATTCACT | TGACTATATT | ATTGATACTG | TCCCTGTTGG | 5640 |
| CCATCCTCTT | GAACCTTATC | TTTCTTTGCT | TAAAATTGAT | GGCAAACTTA | TCTTGATGGG | 5700 |
| AGTTATCAAC | ACCCCCTTGC | AATTTATCTC | CCCCATGGTT | ATGCTCGGTA | AGTCATTTAA | 5760 |
| CTTATTTACG | CTGACAGTGT | AACACGTTCG | GACGAAATGC | ATTATTACAA | CAAGTTAAAA | 5820 |
| TTGGTTTCTA | ACAATATATC | GTGTTAGTAC | TTGCTCTAAA | AAGTCGATTG | AAAATTTAAA | 5880 |
| CGTTGAATTT | GTCTATATAT | GAAAAAGAT | AGAACAAAAG | GATTGGAAGA | GTGGTCATTT | 5940 |
| TAGTCAATGA | AAGCCATGAT | TTGTTGAAAT | ATGCAGGTGC | CATTGGTCTA | TTTTTGCGGC | 6000 |
| ATAATAATGT | TATGAGCAGA | ATTAATATAT | AGACAAATTC | TAGGCTTGTA | GGGTTGTGTT | 6060 |
| ATTTAAGGAA | CCATGTCTGC | AATAATGGAC | TGCAATAACA | ACAGAGACCA | TACACGTATT | 6120 |
| AAAGCCAATG | TATTTGATTA | ACATTTGTTT | AATGCAACCT | CTTATTACTA | TTATGTTTTA | 6180 |
| AGATTTTTTA | AGCACAGACA | GTGTGTAAGT | TTTTTATAC | CATCAAGCAA | AGTTGATATA | 6240 |
| TTCCGAAAAG | AAAAGTTGAT | GTACAATAAT | AGATAACATT | TCATTAGTGT | GGTATGGTAA | 6300 |
| TTTGAAAGTA | GTACTCGGTA | TAATTTTCA | TTTACATTG | TCGGCGTATA | TAACTTTTAG | 6360 |
| ACTTTATTAT | TATGATCAGG | GAGAAAGAGC | ATCACAGGAA | GCTTATTGG | TAGCATGAAG | 6420 |
| GAAACAGAGG | AAATGCTAGA | TTTCTGCAAA | GAGAAAGGTG | TGACTTCACA | GATTGAGATA | 6480 |
| GTGAAAATGG | ATTATATCAA | CACTGCAATG | GAGAGGTTGG | AGAAAAATGA | TGTGAGGTAC | 6540 |
| AGATTTGTGG | TTGATGTTAT | TGGAAGCAAG | CTTGACCAGT | AATTATATTA | CACAAGAAAA | 6600 |
| ACAACATGGA | ATGGTTCACT | ATTATACAAG | GCTGTGAGAA | TACTAAACTT | TGATGTCGTC | 6660 |
| TTTTGTATCC | TTTTGTTTTA | TTTGCCACCT | GTATTTCTT | ATTTGGTGAT | CGAGAGTGAC | 6720 |
| GTTATGTAT | TATTTTCTTT | CTTCAAAACA | ATTAATGTA | TGAATTTGGA | TGTTGGTGAC | 6780 |
| GATTTTGAAA | TATACCAACC | AAAACTTTGT | TTGGTACGTG | AAGCTATCTC | CACTTCTCGT | 6840 |
| GACTAGGGTG | TCGATCCATC | TTTAAATCGA | TTAACCG | | | 6877 |